(12) United States Patent
Lehmann et al.

(10) Patent No.: US 8,043,284 B2
(45) Date of Patent: Oct. 25, 2011

(54) CRYOSURGICAL CATHETER

(75) Inventors: John W. Lehmann, Wayland, MA (US);
Dan Wittenberger, L'ile Bizard (CA);
Claudia Luckge, L'ile Bizard (CA);
Jean-Pierre Lalonde, Candiac (CA);
Cristian Petre, Fabreville (CA);
Domenic Santoianni, Kirkland (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 0 days.

(21) Appl. No.: 12/792,376

(22) Filed: Jun. 2, 2010

(65) Prior Publication Data
US 2010/0286677 A1 Nov. 11, 2010

Related U.S. Application Data

(63) Continuation of application No. 11/224,370, filed on Sep. 12, 2005, now Pat. No. 7,753,905, which is a continuation of application No. 10/657,922, filed on Sep. 9, 2003, now Pat. No. 6,942,659, which is a continuation of application No. 10/050,452, filed on Jan. 16, 2002, now Pat. No. 6,669,689, which is a continuation of application No. 09/845,535, filed on Apr. 30, 2001, now Pat. No. 6,629,972, which is a continuation of application No. 09/201,071, filed on Nov. 30, 1998, now Pat. No. 6,235,019, which is a continuation-in-part of application No. 08/893,825, filed on Jul. 11, 1997, now Pat. No. 5,899,899, which is a continuation-in-part of application No. 08/807,382, filed on Feb. 27, 1997, now Pat. No. 5,899,898.

(51) Int. Cl.
*A61B 18/02* (2006.01)

(52) U.S. Cl. .................. 606/23; 606/21; 606/22
(58) Field of Classification Search ............... 606/20–24
See application file for complete search history.

(56) References Cited

U.S. PATENT DOCUMENTS

| | | | |
|---|---|---|---|
| 3,903,871 A | 9/1975 | Chisum et al. | 128/2 T |
| 3,938,514 A | 2/1976 | Boucher | 128/232 |
| 4,029,099 A | 6/1977 | Fifield | 128/295 |
| 4,176,662 A | 12/1979 | Frazer | 128/6 |
| 4,202,336 A | 5/1980 | van Gerven | |
| 4,375,220 A | 3/1983 | Matvias | 128/804 |
| 4,411,656 A | 10/1983 | Cornett, III | 604/212 |
| 4,509,370 A | 4/1985 | Hirschfeld | 73/705 |
| 4,620,769 A | 11/1986 | Tsuno | 350/96.26 |
| 4,660,571 A | 4/1987 | Hess et al. | 128/784 |
| 4,664,120 A | 5/1987 | Hess | 128/642 |
| 4,686,996 A | 8/1987 | Ulbrich | 128/642 |
| 4,690,155 A | 9/1987 | Hess | 128/786 |
| 4,699,147 A | 10/1987 | Chilson et al. | 128/642 |
| 4,704,104 A | 11/1987 | Christensen | 604/205 |
| 4,709,698 A | 12/1987 | Johnston et al. | 128/303.12 |
| 4,725,267 A | 2/1988 | Vaillancourt | 604/192 |
| 4,754,752 A | 7/1988 | Ginsburg et al. | 128/303.12 |

(Continued)

FOREIGN PATENT DOCUMENTS
GB 002163655 A 3/1986
(Continued)

*Primary Examiner* — Roy Gibson
(74) *Attorney, Agent, or Firm* — Christopher & Weisberg, P.A.

(57) ABSTRACT

A cryogenic catheter includes an outer flexible member having at least one cryogenic fluid path through the flexible member. The at least one fluid path is defined by a plurality of flexible members disposed within the outer flexible member.

19 Claims, 13 Drawing Sheets

U.S. PATENT DOCUMENTS

| | | | |
|---|---|---|---|
| 4,776,349 A | 10/1988 | Nashef et al. | 128/786 |
| 4,787,882 A | 11/1988 | Claren | 604/4 |
| 4,813,425 A | 3/1989 | Malis | 128/642 |
| 4,823,790 A * | 4/1989 | Alperovich et al. | 606/24 |
| 4,850,351 A | 7/1989 | Herman et al. | |
| 4,945,912 A | 8/1990 | Langberg | 128/642 |
| 4,946,440 A | 8/1990 | Hall | 604/95 |
| 4,979,948 A | 12/1990 | Geddes et al. | 606/33 |
| 4,998,933 A | 3/1991 | Eggers et al. | 606/41 |
| 5,007,437 A | 4/1991 | Sterzer | 428/786 |
| 5,010,894 A | 4/1991 | Edhag | 128/785 |
| 5,015,240 A | 5/1991 | Soproni et al. | 604/192 |
| 5,078,713 A | 1/1992 | Varney | 606/23 |
| 5,100,388 A | 3/1992 | Behl et al. | 604/113 |
| 5,139,496 A | 8/1992 | Hed | 606/23 |
| 5,147,355 A | 9/1992 | Friedman et al. | 606/23 |
| 5,168,880 A | 12/1992 | Sogawa et al. | |
| 5,205,298 A | 4/1993 | Hurst | 128/844 |
| 5,224,943 A | 7/1993 | Goddard | 606/20 |
| 5,228,442 A | 7/1993 | Imran | 128/642 |
| 5,231,995 A | 8/1993 | Desai | 128/784 |
| 5,281,213 A | 1/1994 | Milder et al. | 606/15 |
| 5,281,215 A | 1/1994 | Milder | 606/20 |
| 5,293,869 A | 3/1994 | Edwards et al. | 128/642 |
| 5,314,408 A | 5/1994 | Salmon et al. | 604/22 |
| 5,327,881 A | 7/1994 | Greene | 128/11 |
| 5,334,181 A | 8/1994 | Rubinsky et al. | 606/22 |
| 5,342,295 A | 8/1994 | Imran | 604/43 |
| 5,363,882 A | 11/1994 | Chikama | 138/118 |
| 5,364,353 A | 11/1994 | Corfitsen et al. | |
| 5,403,309 A | 4/1995 | Coleman et al. | 606/20 |
| 5,409,469 A | 4/1995 | Schaerf | 604/282 |
| 5,423,807 A | 6/1995 | Milder | 606/20 |
| 5,452,582 A | 9/1995 | Longsworth | 62/51.2 |
| 5,466,222 A | 11/1995 | Ressemann et al. | 604/96 |
| 5,487,385 A | 1/1996 | Avitall | 128/642 |
| 5,520,682 A | 5/1996 | Baust et al. | 606/24 |
| 5,545,200 A | 8/1996 | West et al. | 607/122 |
| 5,569,161 A | 10/1996 | Ebling et al. | 600/121 |
| 5,575,773 A | 11/1996 | Song et al. | 604/110 |
| 5,624,392 A | 4/1997 | Saab | 604/43 |
| 5,669,870 A | 9/1997 | Elist | 600/40 |
| 5,766,192 A | 6/1998 | Zacca | |
| 5,769,702 A | 6/1998 | Hanson | 454/63 |
| 5,792,105 A | 8/1998 | Lin et al. | 604/96 |
| 5,800,482 A | 9/1998 | Pomeranz et al. | 607/101 |
| 5,810,802 A | 9/1998 | Panescu et al. | 606/31 |
| 5,876,324 A | 3/1999 | Trouchine | 600/38 |
| 5,957,963 A | 9/1999 | Dobak, III | 607/104 |
| 6,001,117 A | 12/1999 | Huxel et al. | 606/191 |
| 6,004,269 A | 12/1999 | Crowley et al. | |
| 6,033,426 A | 3/2000 | Kaji | 606/213 |
| 6,096,068 A | 8/2000 | Dobak, III et al. | 607/105 |
| 6,106,518 A | 8/2000 | Wittenberger et al. | 606/23 |
| 6,149,677 A | 11/2000 | Dobak, III | 607/106 |
| 6,162,171 A | 12/2000 | Ng et al. | 600/141 |
| 6,190,348 B1 | 2/2001 | Tiemann et al. | 604/15 |
| 6,224,624 B1 | 5/2001 | Lasheras et al. | 607/105 |
| 6,235,019 B1 | 5/2001 | Lehmann et al. | 606/22 |
| 6,238,371 B1 | 5/2001 | Himbert et al. | 604/187 |
| 6,238,428 B1 | 5/2001 | Werneth et al. | 607/105 |
| 6,245,095 B1 | 6/2001 | Dobak, III et al. | 607/105 |
| 6,248,089 B1 | 6/2001 | Porat | 604/17 |
| 6,248,096 B1 | 6/2001 | Dwork et al. | 604/349 |
| 6,251,130 B1 | 6/2001 | Dobak, III et al. | 607/105 |
| 6,254,626 B1 | 7/2001 | Dobak, III et al. | 607/105 |
| 6,270,482 B1 | 8/2001 | Rosoff et al. | 604/200 |
| 6,270,488 B1 | 8/2001 | Johnson et al. | 604/403 |
| 6,283,294 B1 | 9/2001 | Thorball et al. | 206/438 |
| 6,312,452 B1 | 11/2001 | Dobak, III et al. | 607/105 |
| 6,315,761 B1 | 11/2001 | Shcherbina et al. | 604/216 |
| 6,319,235 B1 | 11/2001 | Yoshino | 604/216 |
| 6,319,248 B1 | 11/2001 | Nahon | 606/22 |
| 2001/0001830 A1 | 5/2001 | Dobak, III et al. | 607/105 |
| 2001/0001831 A1 | 5/2001 | Dobak, III et al. | 607/105 |
| 2001/0002442 A1 | 5/2001 | Dobak, III et al. | 607/105 |
| 2001/0011184 A1 | 8/2001 | Dobak, III et al. | 607/105 |
| 2001/0011185 A1 | 8/2001 | Dobak, III et al. | 607/105 |
| 2001/0016763 A1 | 8/2001 | Lasheras et al. | 607/105 |
| 2001/0021865 A1 | 9/2001 | Dobak, III et al. | 607/105 |
| 2001/0021866 A1 | 9/2001 | Dobak, III et al. | 607/105 |
| 2001/0029394 A1 | 10/2001 | Dobak, III et al. | 607/105 |
| 2001/0047138 A1 | 11/2001 | Kokate et al. | |

FOREIGN PATENT DOCUMENTS

| | | |
|---|---|---|
| JP | 402095364 A | 4/1990 |
| JP | 405293077 A | 11/1993 |
| WO | WO 98/17187 | 4/1998 |

* cited by examiner

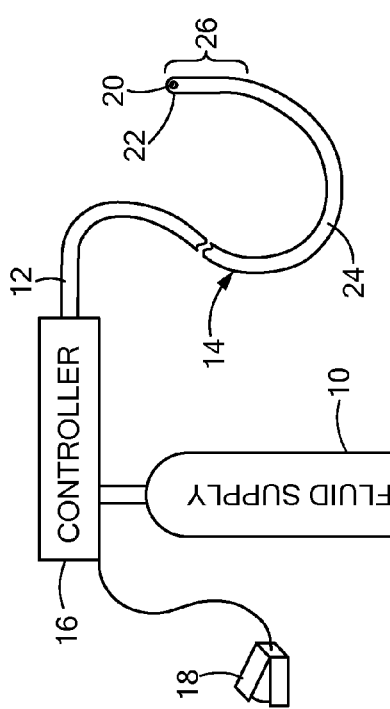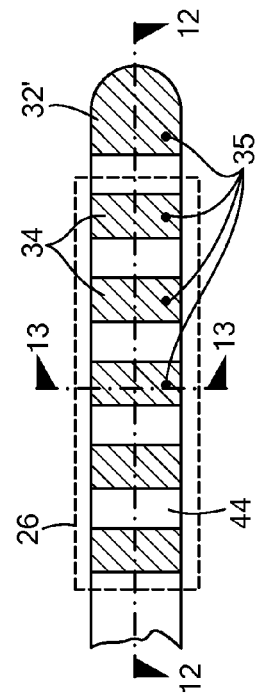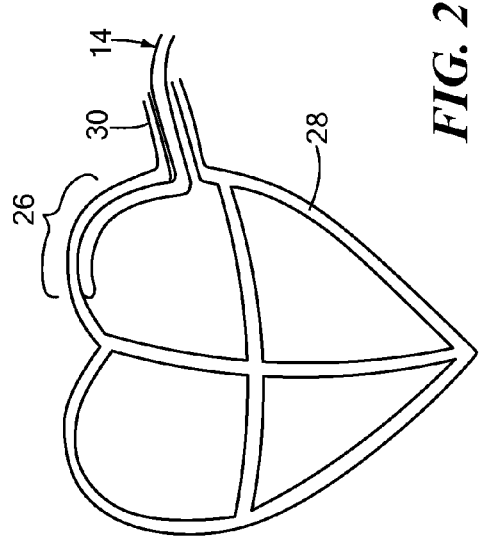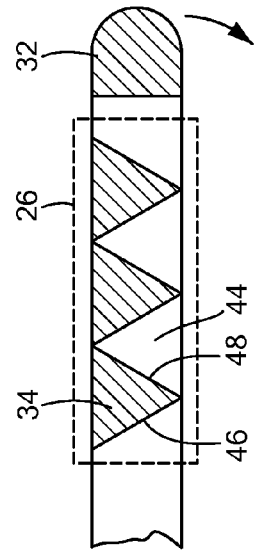

|  | PRESS. [psi] | TEMPERATURE [°C] | | | |
|---|---|---|---|---|---|
|  |  | TIP | RING 1 | RING 2 | RING 3 |
| Test I |  |  |  |  |  |
|  | 230 | -45 | 6 | 16 | 13 |
|  | 250 | -45 | -36 | 3 | 1 |
|  | 270 | -43 | -43 | -19 | -20 |
|  | 290 | -40 | -47 | -23 | -22 |
|  | 310 | -40 | -47 | -32 | -25 |
|  | 330 | -39 | -47 | -38 | -27 |
|  | 350 | -39 | -47 | -47 | -31 |
|  | 370 | -40 | -47 | -48 | -45 |
|  | 390 | -39 | -47 | -48 | -49 |
|  | 410 | -36 | -46 | -47 | -49 |
|  | 430 | -36 | -46 | -48 | -49 |
| Test II |  |  |  |  |  |
|  | 235 | -50 |  |  |  |
|  | 275 | -51 | -52 | -4 | 6 |
|  | 300 | -44 | -50 | -53 | -2 |
|  | 325 | -43 | -51 | -52 | -24 |
|  | 350 | -43 | -50 | -51 | -33 |
|  | 375 | -42 | -49 | -50 | -52 |
|  | 400 | -40 | -49 | -50 | -53 |
|  | 425 | -39 | -48 | -49 | -51 |
|  | 449 | -37 | -47 | -48 | -50 |
| Test III |  |  |  |  |  |
|  | 235 | -48 | -40 | 20 | 25 |
|  | 275 | -48 | -42 | 0 | 5 |
|  | 300 | -47 | -47 | -38 | -8 |
|  | 325 | -45 | -49 | -44 | -25 |
|  | 350 | -42 | -51 | -51 | -35 |
|  | 375 | -41 | -49 | -52 | -51 |
|  | 400 | -38 | -47 | -48 | -52 |
|  | 425 | -38 | -47 | -48 | -53 |
|  | 449 | -36 | -47 | -47 | -50 |

*FIG. 19*

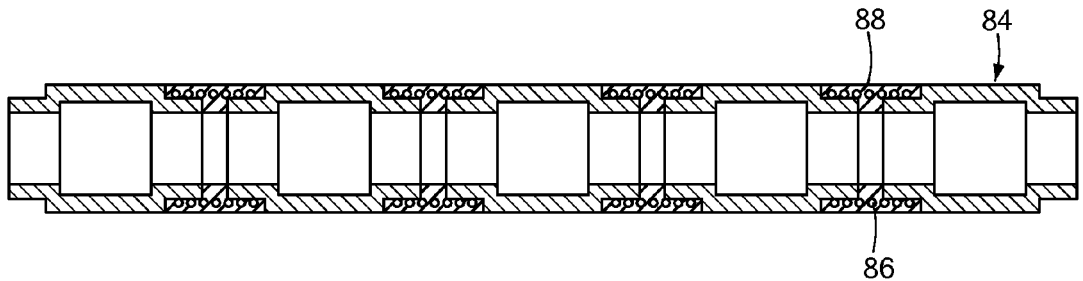
FIG. 20
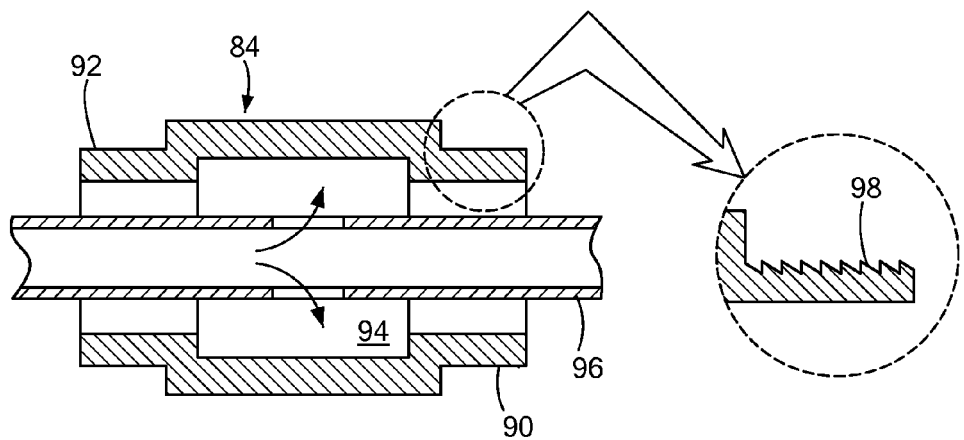
FIG. 21  FIG. 22
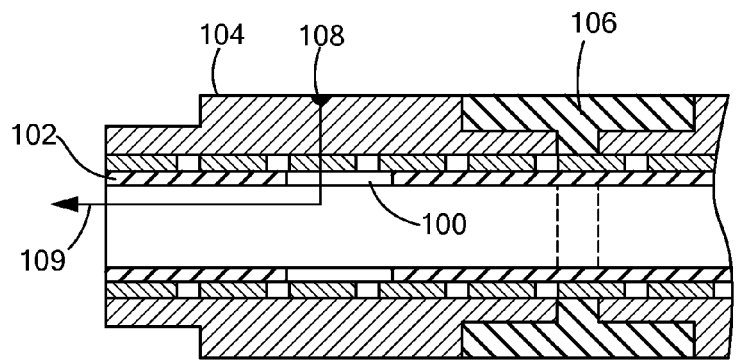
FIG. 23

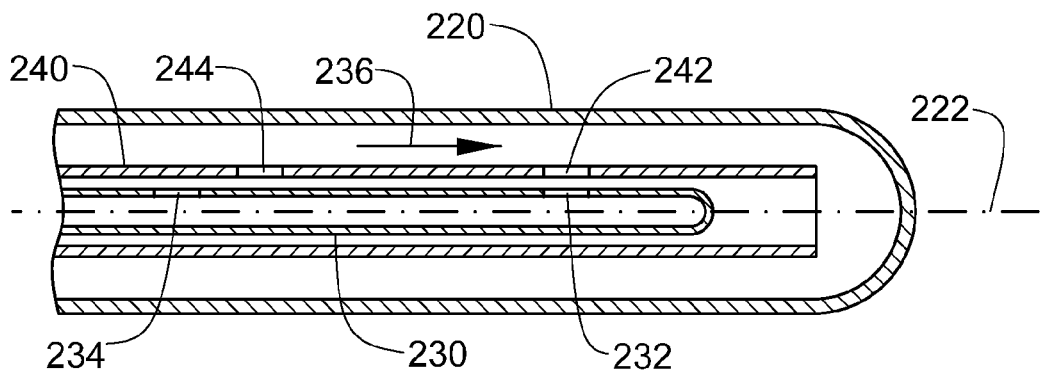
*FIG. 27*
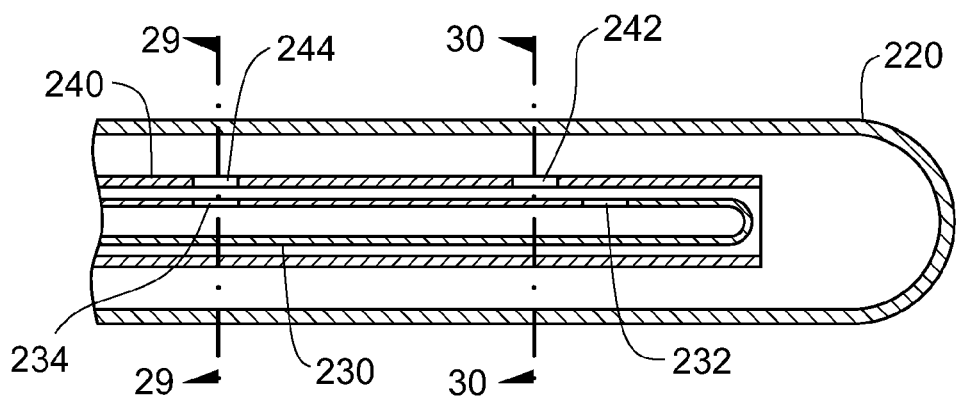
*FIG. 28*
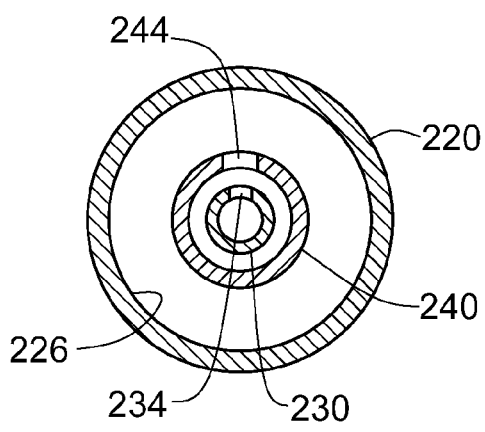 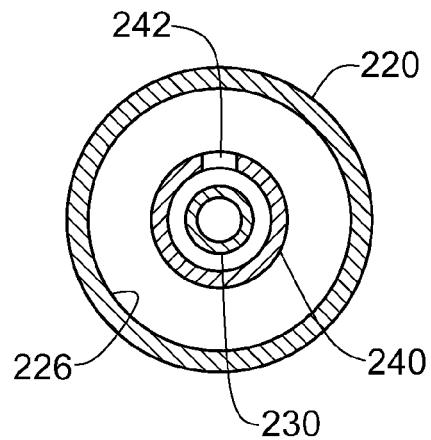
*FIG. 29*  *FIG. 30*

CRYOSURGICAL CATHETER

CROSS-REFERENCE TO RELATED APPLICATION

This application is a Continuation of and claims priority from application Ser. No. 11/224,370, filed Sep. 12, 2005 by John W. Lehmann, et al., entitled CRYOSURGICAL CATHETER, now U.S. Pat. No. 7,753,905, which is a Continuation of and claims priority from application Ser. No. 10/657,922, filed Sep. 9, 2003, by John W. Lehmann, et al., entitled CRYOSURGICAL CATHETER, now issued U.S. Pat. No. 6,942,659, issued Sep. 13, 2005, which application is a continuation of and claims priority from application Ser. No. 10/050,452, filed Jan. 16, 2002, by John W. Lehmann, et al., entitled CRYOSURGICAL CATHETER, now issued U.S. Pat. No. 6,669,689, issued Dec. 30, 2003, which application is a continuation of and claims priority from application Ser. No. 09/845,535, filed Apr. 30, 2001, by John W. Lehmann, et al., entitled CRYOSURGICAL CATHETER, now issued U.S. Pat. No. 6,629,972, issued Oct. 7, 2003, which application is a continuation of and claims priority from U.S. patent application Ser. No. 09/201,071, filed Nov. 30, 1998, by John W. Lehmann, et al., entitled CRYOSURGICAL CATHETER, now issued U.S. Pat. No. 6,235,019, issued May 22, 2001, which application is a continuation-in-part of and claims priority from U.S. patent application Ser. No. 08/893,825, filed Jul. 11, 1997, by Steven G. Arless, et al., entitled CRYOSURGICAL LINEAR ABLATION STRUCTURE, now issued U.S. Pat. No. 5,899,899, issued May 4, 1999, which application is a continuation-in-part of and claims priority from U.S. patent application Ser. No. 08/807,382, filed Feb. 27, 1997, by Steven G. Arless, et al., entitled CRYOSURGICAL LINEAR ABLATION, now U.S. Pat. No. 5,899,898, issued May 4, 1999, all of which are incorporated herein by reference.

STATEMENT REGARDING FEDERALLY SPONSORED RESEARCH

Not Applicable

FIELD OF THE INVENTION

The invention relates to catheters, and more particularly to cryosurgical catheters used for tissue ablation.

BACKGROUND OF THE INVENTION

Many medical procedures are performed using minimally invasive surgical techniques, wherein one or more slender implements are inserted through one or more small incisions into a patient's body. With respect to ablation, the surgical implement can include a rigid or flexible structure having an ablation device at or near its distal end that is placed adjacent to the tissue to be ablated. Radio frequency energy, microwave energy, laser energy, extreme heat, and extreme cold can be provided by the ablation device to kill the tissue.

With respect to cardiac procedures, a cardiac arrhythmia can be treated through selective ablation of cardiac tissue to eliminate the source of the arrhythmia. A popular minimally invasive procedure, radio frequency (RF) catheter ablation, includes a preliminary step of conventional electrocardiographic mapping followed by the creation of one or more ablated regions (lesions) in the cardiac tissue using RF energy. Multiple lesions are frequently required because the effectiveness of each of the proposed lesion sites cannot be predetermined due to limitations of conventional electrocardiographic mapping. Often, five lesions, and sometimes as many as twenty lesions may be required before a successful result is attained. Usually only one of the lesions is actually effective; the other lesions result in unnecessarily destroyed cardiac tissue.

Deficiencies of radio frequency ablation devices and techniques have been overcome by using cold to do zero degree or ice mapping prior to creating lesions, as taught in U.S. Pat. Nos. 5,423,807; and 5,281,213; and 5,281,215. However, even though combined cryogenic mapping and ablation devices permit greater certainty and less tissue damage than RF devices and techniques, both the cryogenic and the RF devices are configured for spot or roughly circular tissue ablation.

Spot tissue ablation is acceptable for certain procedures. However, other procedures can be more therapeutically effective if multiple spot lesions along a predetermined line, or a single elongate or linear lesion is created in a single ablative step. Radio frequency ablation devices are known to be able to create linear lesions by dragging the ablation tip along a line while it is active. However, no cryogenic devices are known that are optimized for, or which are even minimally capable of, creating an elongate lesion.

SUMMARY OF THE INVENTION

The present invention provides a cryogenic catheter having an elongate outer member and a plurality of inner members disposed within the elongate outer member. The inner members have a plurality of controllable openings formed thereon for the selective release of cryogenic fluid. A plurality of electrode members are disposed on an external surface of the outer member. The inner members may be positioned in a staggered configuration or alternatively at least one inner member may be disposed within another inner member. In such a configuration, one of the inner members may be slidable or rotatable to the other.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 1 is a schematic illustration of an embodiment of a cryosurgical system in accordance with the invention;

FIG. 2 is a schematic depiction of the chambers of the heart showing placement of the catheter of FIG. 1;

FIG. 3 illustrates the tip region of one embodiment of the catheter in accordance with the invention;

FIG. 4 illustrates an alternative embodiment of the catheter of FIG. 3;

FIG. 19 is a table illustrating cooling performance of a catheter in accordance with the invention;

FIG. 20 is a sectional view of another catheter embodiment;

FIG. 21 is a sectional view of a portion of the catheter of FIG. 20;

FIG. 22 is a detailed view of an area of the catheter portion illustrated in FIG. 21;

FIG. 23 is an illustration of yet another catheter embodiment;

FIG. 27 illustrates yet still another embodiment of the catheter;

FIG. 28 illustrates the catheter of FIG. 27 in a second configuration;

FIG. 29 is a sectional view of the catheter of FIG. 28 taken along line 29-29;

FIG. 30 is a sectional view of the catheter of FIG. 28 taken along line 30-30;

DETAILED DESCRIPTION OF THE INVENTION

Figure 5:
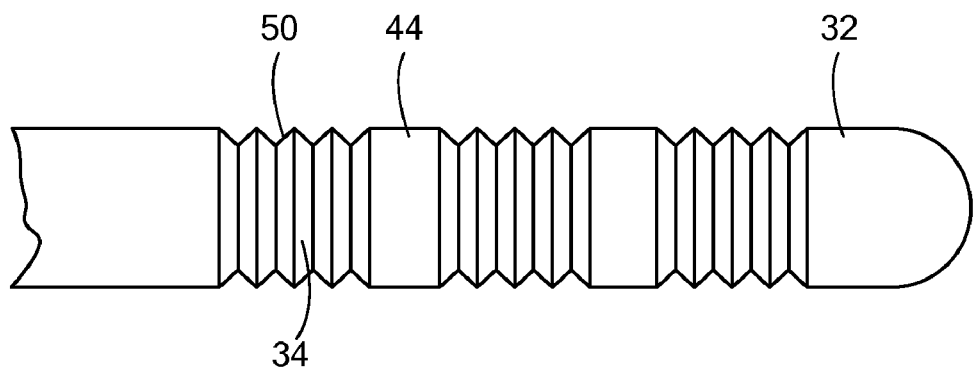
FIG. 5 illustrates yet another embodiment of the catheter.

FIG. 1 is a schematic illustration of a cryosurgical system in accordance with the invention. The system includes a supply of cryogenic or cooling fluid 10 in communication with the proximal end 12 of a flexible catheter 14. A fluid controller 16 is interposed or in-line between the cryogenic fluid supply 10 and the catheter 14 for regulating the flow of cryogenic fluid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals. In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example a temperature sensor can be placed at a point proximate the distal end 22 of the catheter and other temperature sensors 20 can be placed at spaced intervals between the distal end of the catheter and another point that is between the distal end and the proximal end.

The cryogenic fluid can be in a liquid or a gas state. An extremely low temperature can be achieved within the catheter, and more particularly on the surface of the catheter by cooling the fluid to a predetermined temperature prior to its introduction into the catheter, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50-50 mixture of difluoromethane & pentafluoroethane sold by Allied Signal), and CFC's such as DuPont's Freon. Exemplary gasses include nitrous oxide, and carbon dioxide.

The catheter 14 includes a flexible member 24 having a thermally-transmissive region 26 and a fluid path through the flexible member to the thermally-transmissive region. A fluid path is also provided from the thermally-transmissive region to a point external to the catheter, such as the proximal end 12. Although described in greater detail below, exemplary fluid paths can be one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat.

For example, a metal structure exposed (directly or indirectly) to the cryogenic fluid path is considered a thermally-transmissive region 26 even if an adjacent polymeric or latex catheter portion also permits heat transfer, but to a much lesser extent than the metal. Thus, the thermally-transmissive region 26 can be viewed as a relative term to compare the heat transfer characteristics of different catheter regions or structures.

Furthermore, while the thermally-transmissive region 26 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process without having to relocate the catheter one or more times or drag it across tissue. Additional details of the thermally-transmissive region 26 and the thermal transfer process are described in greater detail below.

In exemplary embodiments of the invention, the thermally-transmissive region 26 of the catheter 14 is deformable. An exemplary deformation is from a linear configuration to an arcuate configuration and is accomplished using mechanical and/or electrical devices known to those skilled in the art. For example, a wall portion of the flexible member 24 can include a metal braid to make the catheter torqueable for overall catheter steering and placement. Additionally, a cord, wire or cable can be incorporated with, or inserted into, the catheter for deformation of the thermally transmissive region 26.

The cryogenic system of FIG. 1 is better understood with reference to its use in an operative procedure as shown in FIG. 2. Following the determination of a proposed lesion site within a heart chamber 28, for example, the catheter 14 is directed through a blood vessel 30 to a region within the heart, such as an atrial or ventricular chamber, where the lesion will be made. The thermally-transmissive region 26 is placed proximate to the tissue to be ablated. The thermally-transmissive region of the catheter may be deformed to conform to the curvature of the tissue before, during, or after placement against the tissue. The controller 16 allows or causes cryogenic fluid to flow from the cryogenic fluid supply 10 to the fluid path in the catheter 14 and thence to the thermally-transmissive region 26 to ablate the desired area or to cold map along the same tissue area. In one embodiment (e.g., FIG. 12) a first conduit is concentric within a second conduit and cooling fluid travels to a thermally-transmissive region proximate a closed distal end of the catheter through a first conduit (fluid path) and is exhausted from the catheter through the second conduit (fluid path).

Having described the function of the cryogenic catheter 14 and its use in a system context, several exemplary embodiments of the thermally-transmissive region 26 of the catheter are now described in greater detail. FIGS. 3, 4, 5, 12-16 and 18 illustrate embodiments of the catheter, or portions thereof, having two or more thermally-transmissive segments in a spaced-apart relationship. Each of the illustrated catheters includes a closed tip 32 that can include a thermally-transmissive material.

Figure 13:
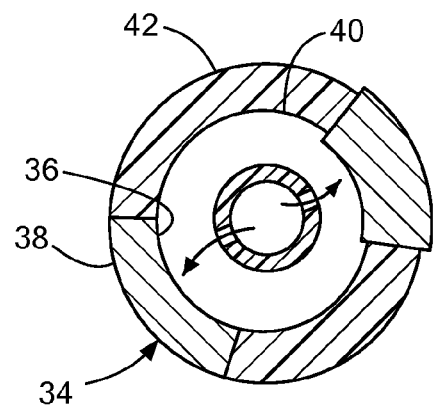
FIG. 13 is a sectional view of the catheter of FIG. 3 taken along line 13-13.
Figure 14:
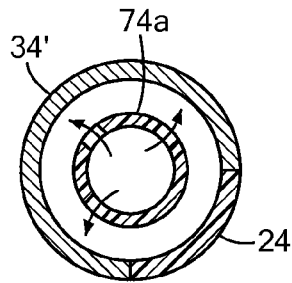
FIGS. 14-16 are sectional views of additional catheter embodiments.
Figure 15:
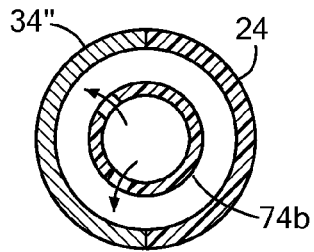
Figure 16:
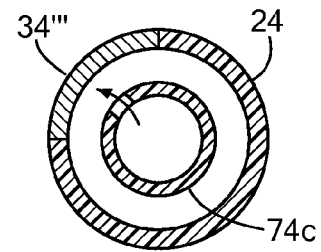

Referring specifically to the embodiment depicted in FIG. 3, multiple thermally-transmissive elements 34 are integral with a distal portion of a catheter. Each of the thermally-transmissive elements 34 includes a first side or face 36 (shown in FIGS. 12 and 13) exposed to a cryogenic fluid path and cryogenic fluid (shown by arrows) and a second side or face 38 exposed to points exterior to the catheter. As shown in FIG. 13, the first side 36 and/or second side 38 of any or all of the thermally-transmissive elements 34 can be substantially flush with, recessed below, or protruding from the inner surface 40 and outer surface 42 of a portion of the catheter. The thermally-transmissive elements 34 are separated by flexible portions of material 44 than can range from slightly less thermally-transmissive than the adjacent thermally-transmissive elements to substantially less thermally-transmissive than the adjacent elements. In the illustrated embodiment of FIG. 3, the thermally-transmissive elements 34 are annular, cylindrical elements which are made of gold-plated copper or bronze. Thermocouples 35 can be associated with one or more of the elements 34 and the tip 32. The thermally-transmissive elements 34 can be completely exposed, embedded, or a combination thereof along the full 360.degree. of the catheter's circumference. In certain applications the thermally-transmissive elements traverse or define less than 360.degree. of the catheter's circumference as shown in FIGS. 14-16 and as described below. The longitudinal width of each thermally-transmissive element 34, the spacing between elements, the material thickness, and the material composition are matched with a selected cryogenic fluid, one or more cryogenic fluid delivery locations within the catheter and fluid delivery pressure to produce overlapping cold regions which produce a linear lesion.

The embodiment illustrated in FIG. 4 is substantially identical to the embodiment of FIG. 3, however, at least one of the thermally-transmissive elements 34 includes a first open end 46 that defines a first plane and a second open end 48 that defines a second plane, wherein the first and second planes intersect to give the annular elements a wedge-like appearance. Such a configuration permits adjacent thermally-transmissive elements 34 to be positioned very closely together, but it can limit the possibilities for deforming the thermally-transmissive region 26, which, in this embodiment, is flexible in the direction indicated by the arrow.

With respect to the embodiments shown in both FIGS. 3 and 4, the thermally-transmissive elements 34 are substantially rigid and are separated and/or joined by a flexible material 44. However, in other embodiments the thermally-transmissive elements 34 are flexible and are interdigitated with either rigid or flexible segments. FIG. 5, for example, illustrates an embodiment of the cryogenic catheter having three thermally-transmissive elements 34 that are flexible. The flexibility is provided by a folded or bellows-like structure 50. In addition to being shapable, a metal bellows can have enough stiffness to retain a selected shape after a deforming or bending step.

Figure 6:
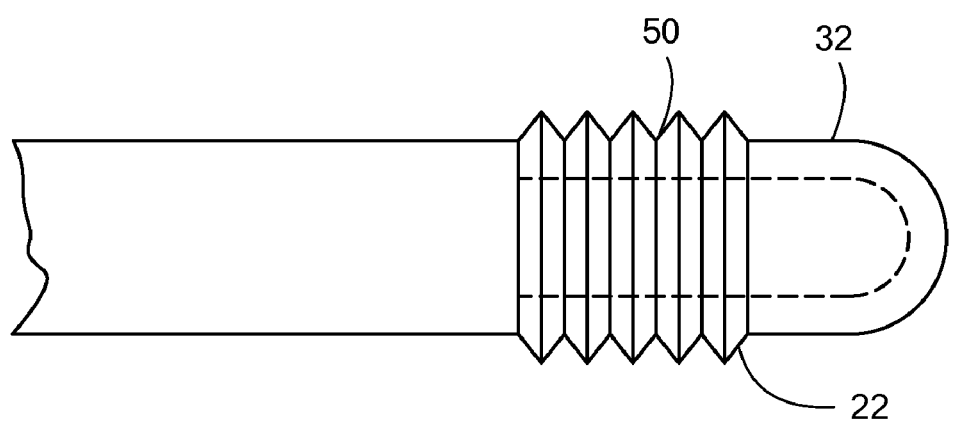
FIG. 6 illustrates a deformable tip for a catheter.

Instead of, or in addition to, flexible, thermally-transmissive elements 34 and/or flexible material 44 between elements, the distal tip 32 (or a portion thereof) can be deformable. For example, FIG. 6 illustrates a tip 32 having thermally-transmissive, flexible, bellows 50.

Figure 7:
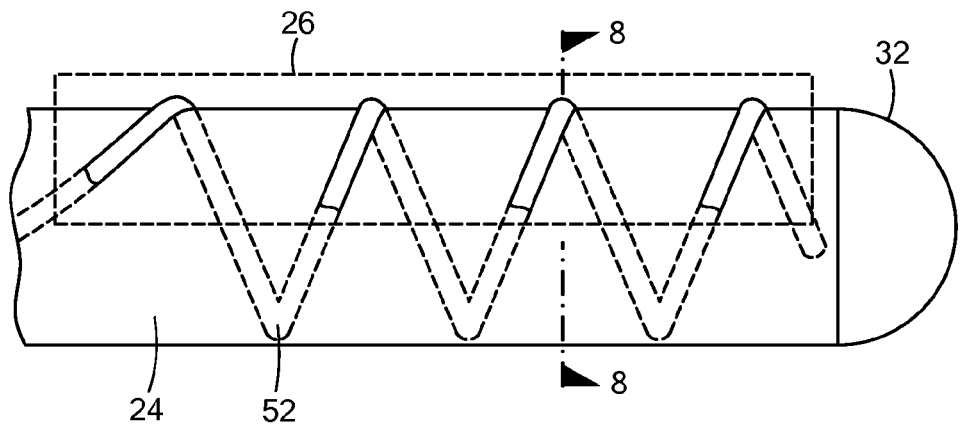
FIG. 7 illustrates yet another embodiment of the catheter.
Figure 8:
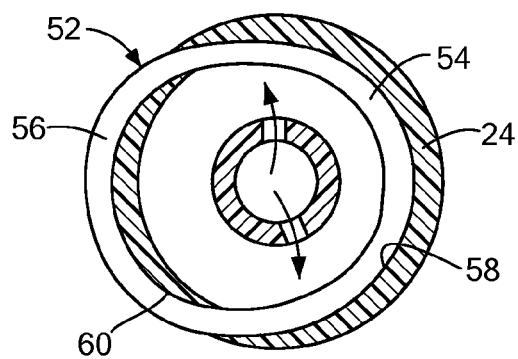
FIG. 8 is a sectional view of the catheter of FIG. 7 taken along line 8-8.

Referring now to FIGS. 7-10, a different approach is shown for providing multiple thermally-transmissive segments in a spaced-apart relationship. FIG. 7 illustrates a catheter embodiment having an elongate, thermally-transmissive region 26 that includes a helical coil 52 at least partially embedded in the flexible member 24. As shown in FIG. 8, at least a first portion 54 of the helical coil 52 is exposed to a fluid path within the flexible member 24 and a second portion 56 of the helical coil is exposed to the exterior of the flexible member. As described above with respect to FIG. 13, the first portion 54 of the coil can be substantially flush with, recessed below, or protruding from an inner surface 58 of the flexible member 24. Similarly, the second portion 56 of the coil 52 can be substantially flush with, recessed below, or protruding from an outer surface 60 of the flexible member 24.

In the embodiment of FIG. 8, the second portion 56 of the coil 52 is exposed along only a portion of the outer circumference of the flexible member 24 to define a longitudinally-elongate, thermally-transmissive region 26. This configuration can be provided by eccentrically mating the helical coil 52 to the catheter so that the longitudinal axis of the coil and the longitudinal axis of the catheter are substantially parallel. The eccentric positioning of the coil 52 provides excellent cooling performance because the surface area available for thermal exchange between the first portion 54 of coil and the cryogenic fluid is greater than the surface area available for thermal exchange between the second portion 56 of the coil and adjacent tissue where cooling power is delivered by each exposed coil portion to provide a linear lesion.

Figure 9:
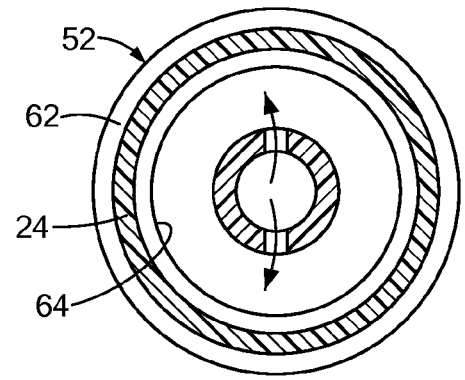
FIG. 9 is a sectional view of an alternative embodiment of the linear ablation catheter illustrated in FIG. 7.

Referring now to FIG. 9, an alternative embodiment is shown wherein a first portion 62 of the coil 52 is exposed around the entire circumference of the flexible member 24, and a second portion 64 is exposed to a fluid path around the inner surface of the flexible member 24. This is achieved by having the longitudinal axis of the helical coil 52 co-axial with the longitudinal axis of the catheter.

Figure 10:
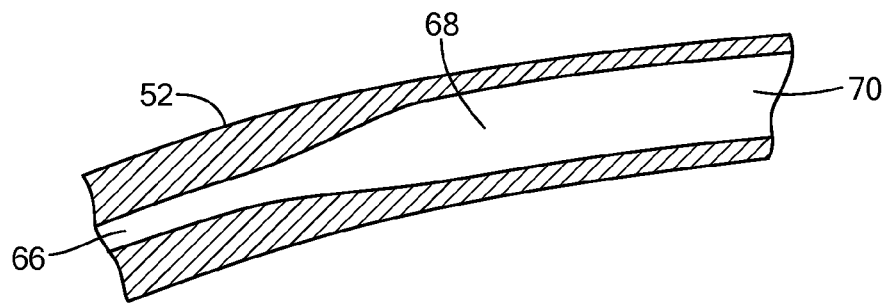
FIG. 10 illustrates an expansion chamber within a portion of a helical coil.

In the embodiments illustrated in FIGS. 7-9, the coil 52 is solid. However, in other embodiments the coil can be an elongate, hollow, gas expansion chamber. For example, FIG. 10 illustrates a portion of a helical coil 52 that includes a passage that defines at least a portion of a fluid path through a flexible member of the catheter. The coil 52 defines a first fluid path diameter at a fluid entry point 66 and a second fluid path diameter that is greater than the first fluid path diameter at a gas expansion or boiling location 68. Gas escaping from a fluid exit point 70 can be exhausted through an open central region of the coil and/or another passage through the flexible member 24.

Figure 11:
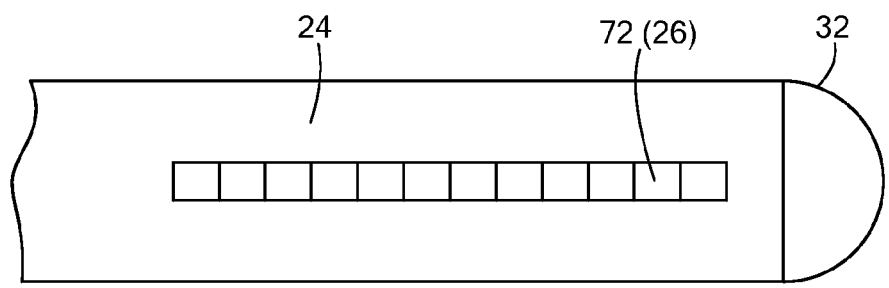
FIG. 11 illustrates a portion of a catheter having an elongate, thermally-transmissive strip.

FIG. 11 illustrates an embodiment of the catheter wherein a continuous, elongate, thermally-transmissive strip 72 is longitudinally integrated with a flexible member 24. The strip can include a bellows-like structure. As described above with respect to other embodiments, a first portion of the strip can be substantially flush with, recessed below, or protrude from the outer surface of the flexible member. Similarly, a second portion of the strip can be substantially flush with, recessed below, or protrude from an inner surface of the flexible member.

Figure 12:
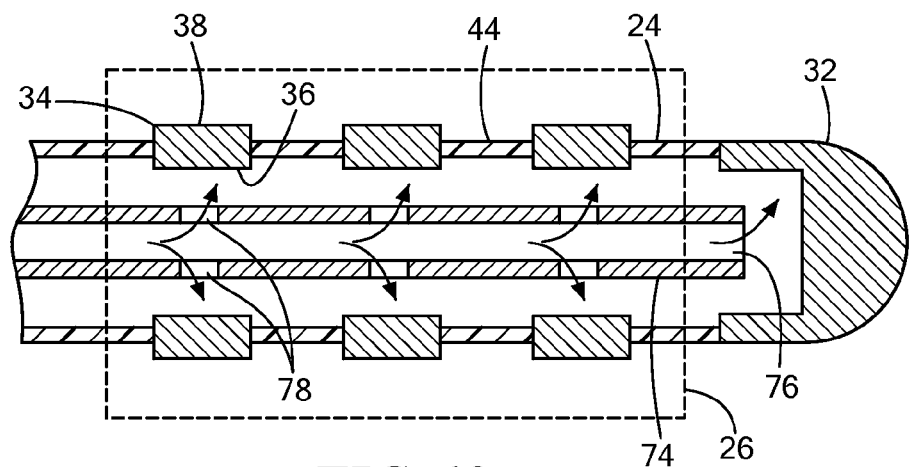
FIG. 12 is a sectional view of the catheter of FIG. 3 taken along line 12-12.

Referring now to FIG. 12, an embodiment of the catheter is illustrated having a second or inner flexible member 74 within a lumen of first or outer flexible member 24, wherein the second flexible member defines a fluid path to the thermally-transmissive region 26. The inner member 74 can include a single opening 76 at or near the tip 32. Cryogenic fluid is expelled from the opening 76 and returns to the proximal end of the catheter along a fluid path defined by the outer wall of the inner member 74 and the inner wall of the outer member 24. This fluid path configuration is also partially illustrated in FIGS. 8, 9, and 13. Alternatively, as also shown in FIG. 12, the inner member 74 can be provided with multiple openings 78 proximate to and/or aligned with the inner face of one or more thermally-transmissive elements 34 to achieve more uniform cooling across the entire elongate, thermally-transmissive region 26.

Referring now to FIGS. 14-16, sectional views of catheter embodiments are illustrated to show alternative configurations for thermally-transmissive elements. The previously described thermally-transmissive elements 34 are arcuate and form complete and continuous 360 degree structures that traverse the complete circumference of the catheter, notwithstanding being flush with, depressed below, or raised above the outermost surface of the flexible member 24. However, the arcuate elements 34', 34", and 34'" illustrated in FIGS. 14-16, respectively, traverse less than 360 degrees of the circumference of the first flexible member and do not form complete loops. For example, in FIG. 14, element 34' defines an approximately 270 degree arc. In FIG. 15 the thermally-transmissive element 34" defines an approximately 180 degree arc; and in FIG. 16, the thermally-transmissive element 34'" defines an approximately 90 degree arc. A catheter can include combinations of element types, such as a complete ring or loop element, a 270 degree element and a 180 degree element as desired to define a thermally transmissive region. In addition to the having applicability with respect to rigid thermally-transmissive elements, the bellows-like elements can also be less than 360 degrees.

The less than 360 degree arcuate elements provide unique functional benefits with respect to thermal transfer and flexibility of the thermally-transmissive region. For example, because the portion of the catheter between the opposing ends of element 34', 34", 34'" does not include a rigid structure, but rather only the resilient material of flexible member 24, the thermally-transmissive region of the catheter can be more tightly curved (gap between ends inward and element facing outward) than it could with complete 360 degree structures, especially if the elements are relatively long longitudinally.

The inner member 74 can be adapted to direct cooling fluid at only the thermally transmissive element(s) and the shape and/or the number of openings for cooling fluid can be configured differently depending on the length of the arc defined by the thermally-transmissive element(s). For example, FIG. 14 illustrates an embodiment of the inner member having three openings opposing the thermally transmissive element 34'; FIG. 15 illustrates two openings for a smaller arc; and FIG. 16 discloses a single opening for an even smaller arc.

Another advantage to providing one or more thermally-transmissive elements that have a less than 360 degree configuration is that limiting the span of the elements to a desired lesion width, or somewhat greater than a desired lesion width, reduces the thermal load on the system and/or permits colder temperatures to be achieved than with respect to a complete 360 degree structure. Unnecessary and perhaps undesirable cooling does not occur at any other location along the catheter except at an elongate region of predetermined width. A similar effect can also be achieved by providing a non-circular 360 degree element or by eccentrically mounting a circular 360 degree element with respect to the flexible member, wherein a portion of the 360 degree element is embedded within the wall of the flexible member or otherwise insulated from the cryogenic fluid path in a manner similar to that shown in FIG. 8.

Figure 17:
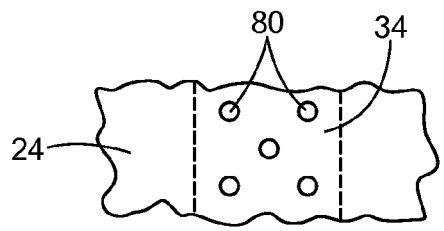
FIG. 17 illustrates an inner face of a flexible catheter member.

Referring now to FIG. 17, a portion of the inner face of an outer flexible member showing in an exemplary embodiment, thermal transfer pins 80 protruding from the inner face of a thermally-transmissive element 34. The pins permit thermal transfer through the flexible member 24. As with the other features of the invention, the pins are equally suitable for complete 360 degree element structures or less than 360 degree structures. Although only pins are shown on any geometric or surface means to increase heat transfer including but not limited to pins, irregularities, channels or surface modifications may be used.

Figure 18:
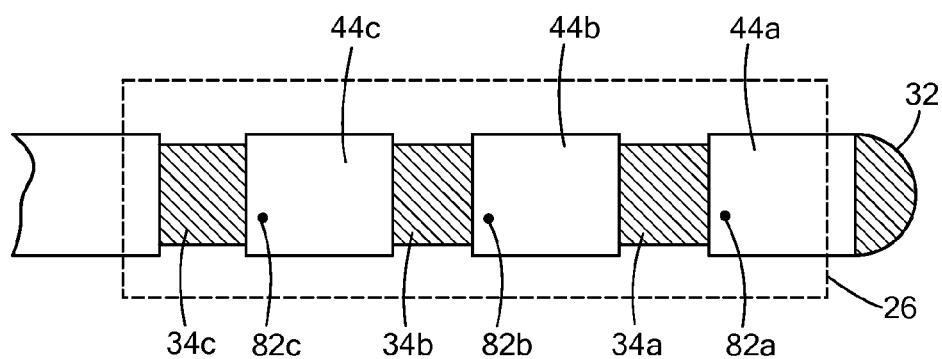
FIG. 18 depicts yet another embodiment of a catheter in accordance with the invention.

Referring now to FIG. 18, yet another embodiment of the catheter is shown wherein rigid metal rings 34a-c are interdigitated with flexible segments 44a-c to define a first flexible member and a thermally-transmissive region approximately one inch in length. A second flexible member is concentric within the first flexible member and has an outlet for cryogenic fluid at its distal end. Thermocouples 82a-c can be associated with one or more of the rings 34a-c.

It has been described above how the thermal loading of a cooling system can be reduced by providing thermally-transmissive elements that span less than 360 degrees. However, the thermal loading can also be reduced by sequentially cooling the thermally-transmissive region. One way to sequentially cool is to modulate the pressure of the cooling fluid along the fluid path through the flexible member. This modulation can be performed by the fluid controller which can be programmed to increase and decrease the pressure of the fluid by predetermined pressure increments over predetermined time intervals. When the cryogenic fluid is a liquid that provides cooling by changing phase from liquid to gas, the change of pressure alters the physical location along the fluid path where the phase change takes place and concomitantly changes the point of coldest temperature along the thermally-transmissive region. Thus, varying the pressure of the fluid can provide a moving ice-formation "front" along the catheter, enabling the creation of a linear lesion.

Therefore, a method of forming an elongate tissue lesion can include the following steps using any of the above described catheters having an elongate, thermally-transmissive region. In a first step a cryogenic fluid is introduced into the flexible member at a first predetermined pressure. Next, the pressure of the cryogenic fluid is incrementally increased within the flexible member until a second predetermined pressure is achieved. Similarly, the pressure of the cryogenic fluid within the flexible member can be decreased incrementally from the second predetermined pressure to the first predetermined pressure, wherein the steps of incrementally increasing and decreasing the pressure define a thermal cycle. Typically, from one to eight thermal cycles are required to achieve a desired therapeutic effect. In an exemplary method, about ten increments of about five seconds in duration are selected and pressure is increased by about 20 to 40 pounds per square inch in each increment. Thus, using this method an elongate lesion can be created in less than 20 minutes.

FIG. 19 is a table that illustrates sequential cooling in a catheter as described above having a thermally-transmissive region that includes a tip and three elements or rings. The table illustrates three tests conducted in a still bath at 37.degree. C., using AZ-20 as the cryogenic fluid. Associated with each pressure increment are measured temperatures at the tip, first ring, second ring, and third ring. The shaded region illustrates the sequential movement of a target temperature range (upper −40's to low −50's) in response to a change in pressure. Although values are only provided for three rings, a similar effect and pattern is obtained with more than three rings or elements.

Turning now to FIG. 20, a thermally-transmissive portion of another embodiment of a medical device or structure such as a catheter is illustrated in a sectional view. The structure can include an inner passage or lumen as described above with respect to other embodiments, but which is not shown in this illustration for purposes of clarity. Thus, the illustrated portion is the outer passage or lumen that defines an elongate ablation region. Thermally-transmissive elements 84, such as gold plated copper, are joined to adjacent elements by resilient connecting elements 86, such as a stainless steel springs welded to the ends of the elements 84. A resilient bio-compatible material 88 covers the connecting elements 86 and the interstices between adjacent thermally-transmissive elements. In an exemplary embodiment, the material 88 is vulcanized silicone. It should be noted in the illustration that the surface of the elements 84 is contiguous and co-planar with the material 88 to provide a smooth outer surface.

FIG. 21 illustrates a single thermally-transmissive element 84 having reduced diameter ends 90 and 92. The wider central portion 94 provides an expansion chamber for gas (shown by arrows) exiting an apertured inner passage 96. FIG. 22 shows additional detail of the end 90 of the element 84. The end 90 is textured, such as by providing serrations 98, to provide a good adhesion surface for the material 88.

Referring now to FIG. 23, a thermally-transmissive portion of yet another embodiment of a flexible cryogenic structure is illustrated in a sectional view. In this embodiment an inner, apertured structure 100 has a flat wire 102 wrapped around it in a spiral manner. Thermally-transmissive segments 104 are disposed upon the wire 102 in a spaced-apart relationship, and a flexible, bio-compatible material 106 fills the interstices between segments 104. A thermocouple 108 can be associated with each segment 104. A wire 109 connects the thermocouple 108 to instrumentation near the proximal end of the structure. The exterior surface of the structure is smooth, and the structure can include 3 to 12 segments 104. In an exemplary embodiment the inner structure 100 is made of PTFE, the material 106 is 33 D Pebax, and the wire 102 is stainless steel or Nitinol. An apertured inner passage (similar to that shown in FIG. 21) is placed within the structure.

Figure 24:
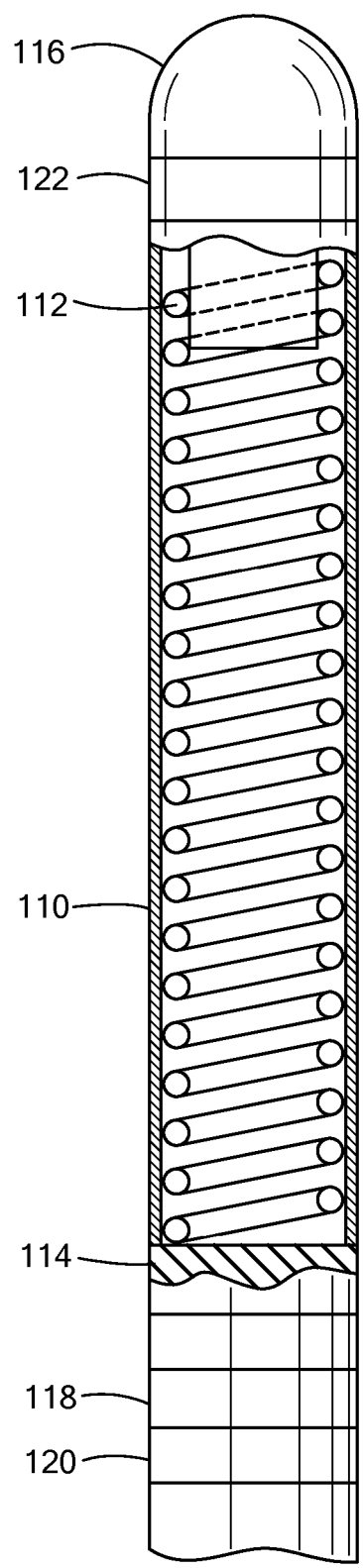
FIG. 24 depicts still another catheter embodiment.

FIG. 24 illustrates still another embodiment of a cryogenic cooling structure that includes a surface or wall 110 including a polymer or elastomer that is thin enough to permit thermal transfer. For example, polyamide, PET, or PTFE having a thickness of a typical angioplasty balloon or less (below 0.006 inches) provides acceptable thermal transfer. However, the thinness of the wall 110 allows it to readily collapse or otherwise deform under vacuum or near vacuum conditions applied to evacuate fluid/gas from the structure. Accordingly, the structure is provided with one or more supporting elements 112 such as a spring. The cooling structure is illustrated in association with a catheter 114 having a closed distal tip 116 and mono or bipolar ECG rings 118, 120, 122. The thermally-transmissive region is approximately 30 mm in length and is effective for thermal transfer over its entire circumference. However, as illustrated in FIG. 11, the thermally-transmissive region can be confined to specific region (s) of the device's circumference.

Figure 25:
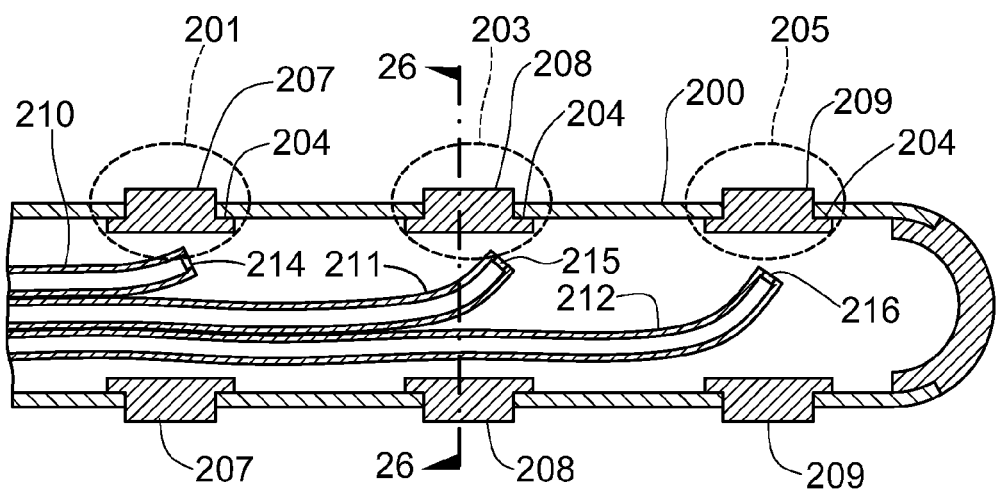
FIG. 25 illustrates yet another embodiment of the catheter.

Referring now to FIG. 25, an embodiment of the catheter is illustrated having three flexible members or injection tubes 210, 211 and 212 disposed within a first or outer flexible member 200. In an exemplary embodiment, the inner flexible members 210, 211 and 212 are arranged in a staggered configuration within the outer flexible member 200. As used herein, term "staggered" may be used to designate both a linearly/axially staggered configuration or alternatively, a rotationally staggered configuration. The flexible members 210, 211 and 212 thus define multiple staggered fluid paths within the outer member 200. In such a configuration, the injection tubes 210, 211 and 212 allow for greater aggregate cooling power as well as the creation of a variety of different cooling/freeze zones 201, 203 and 205 along the length of the outer flexible member 200. In an exemplary embodiment, thermocouples 204 disposed along the outer surface of the outer flexible member 200 may be integrated with an internal feedback loop to provide independent and variable regulation of these freeze zones.

Figure 26:
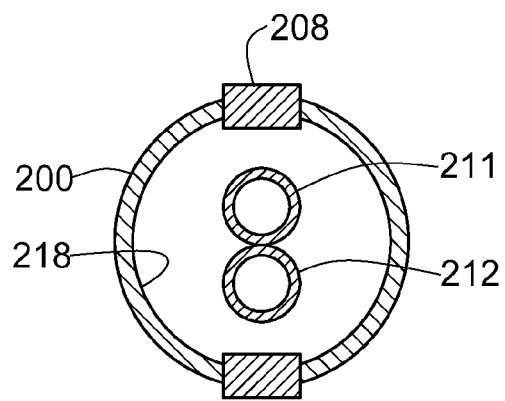
FIG. 26 is a sectional view of the catheter of FIG. 25 taken along line 26-26.

In an exemplary embodiment, the first inner member 210 includes at least one opening 214 positioned proximate an electrode ring member 207. Cryogenic fluid is expelled from the opening 214 and returns to the proximal end of the catheter along a fluid path defined by the inner wall 218 of the outer member 200, as shown in FIG. 26. Similarly, the second inner member 211 includes at least one opening 215 positioned proximate a second electrode ring member 208. Cryogenic fluid is also expelled from the opening 215 and returns to the proximal end of the catheter along the fluid path defined by the inner wall 218 of the outer member 200. Similarly, the third inner member 212 includes at least one opening 216 positioned proximate a third electrode ring member 209.

Alternatively, the catheter can be provided with only two inner members, or four or more inner members, not shown, disposed within the outer member. The inner members would have one or more openings proximate to and/or aligned with the inner face of one or more transmissive elements, as described earlier herein, to achieve different regions of freeze zones across the entire elongate member. Alternatively, all the staggered inner members may be simultaneously provided with cryogenic fluid to create a linear lesion for selected applications. The flow of cooling fluid along the fluid paths through the flexible members can also be alternated in any number of patterns among the multiple inner members to provide a desired cooling pattern such as a discontinuous or a continuous lesion across the entire catheter.

In an exemplary embodiment, a catheter with a plurality of thermally conductive electrode rings would have an underlying injection tube or tubes controlling the release of cryogenic fluid to each electrode. Such a catheter could be placed in the coronary sinus or endocardially along the atrioventricular junction. Once positioned, an electrogram of interest is located using a specific electrode ring on the catheter. Cold-mapping may be performed on the selected location to confirm the correctness of the location. Once, confirmed, the area is cryoablated using the same electrode ring. The same embodiments and others described herein are equally suited to other organs besides the heart and/or any body portion that would benefit from the application of thermal energy.

Referring now to FIG. 27, an embodiment of the catheter is illustrated having an outer member 220 with a fixed injection tube 230 disposed within a slidable sheath or overtube 240 therein. The injection tube and overtube are shown spaced apart for illustrative purposes only. Preferably, the injection tube is sized so that an outer surface of the injection tube engages an inner surface of the overtube while still allowing one member to slide or rotate relative to the other.

The fixed injection tube 230 has multiple openings 232, 234 formed thereon and the slidable overtube also has multiple openings or ports 242, 244 formed thereon. In one configuration shown in FIG. 27, opening 232 on the injection tube 230 coincides or is aligned with opening 242 on the slidable overtube 240. Thus, any fluid exiting the injection tube 230 from opening 232 is able to escape through opening 242.

As the slidable overtube 240 is slid or moved in a first direction as shown by arrow 236 along longitudinal axis 222, opening 232 is covered or blocked by the surface of overtube 240 as now shown in FIG. 28. In a second configuration shown in FIG. 29, opening 234 of injection tube 230 is aligned with opening 244 of overtube 240. In the same configuration, as shown in FIG. 30, opening 242 is not aligned with any opening formed on the surface of injection tube 230. Although only shown in two positions or configurations, the slidable overtube is positionable in any number of positions relative to the fixed injection tube. The overtube may also be used to partially cover the openings on the injection tube to provide for a limited or controlled flow of cryogenic fluid.

Depending on which opening of the injection tube is aligned with the openings formed on the overtube, cryogenic fluid is expelled from the opening and returns to the proximal end of the catheter along a fluid path defined by the inner wall 226 of the outer member 220. The non-aligned opening will not expel fluid since the opening will be blocked. Alternatively, the injection tube and overtube can be provided with three or more openings to achieve multiple cooling/freeze zones along the length of the catheter.

Figure 31:
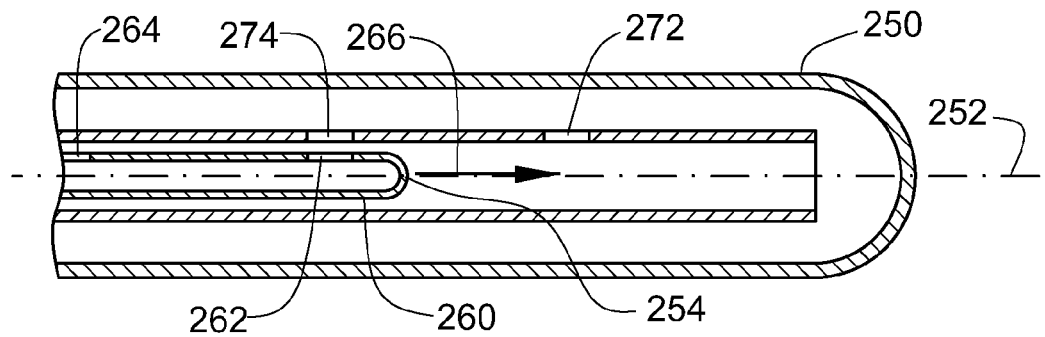
FIG. 31 illustrates yet another embodiment of the catheter.

Referring now to FIG. 31, an embodiment of the catheter is illustrated having a slidable injection tube 260 disposed within a fixed sheath or overtube 270. As shown in FIG. 31, both the injection tube 260 and overtube 270 are disposed within a flexible outer member 250. The slidable injection tube 260 has multiple openings 262, 264 formed thereon which allows for the release of cryogenic fluid. The fixed overtube 270 also has multiple perforations or openings 272, 274 formed thereon which allows for the differential release of fluid as described in more detail below. The injection tube may be further provided with a thermistor 254 disposed proximate the distal end of the tube to provide thermistor feedback. In one embodiment, the openings can be controlled by miniaturized means such as micro or nanovalves.

In a first configuration shown in FIG. 31, opening 262 of the injection tube 260 coincides or is aligned with opening 274 of the fixed overtube 270. As the slidable injection tube 260 is slid or moved in a first direction as shown by arrow 266, opening 262 is then aligned with corresponding opening 272 on the overtube 270 in FIG. 32.

Figure 32:
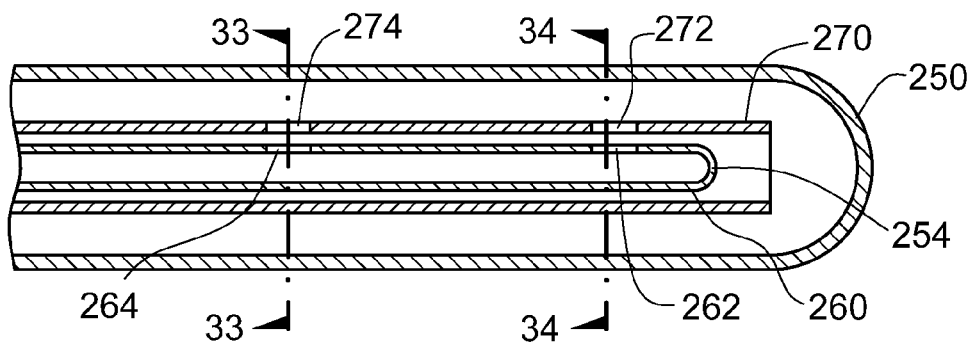
FIG. 32 illustrates the catheter of FIG. 31 in a second configuration.
Figure 33:
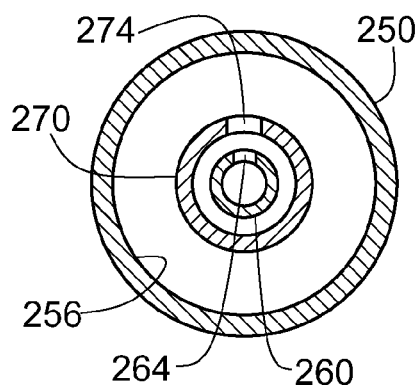
FIG. 33 is a sectional view of the catheter of FIG. 32 taken along line 33-33.
Figure 34:
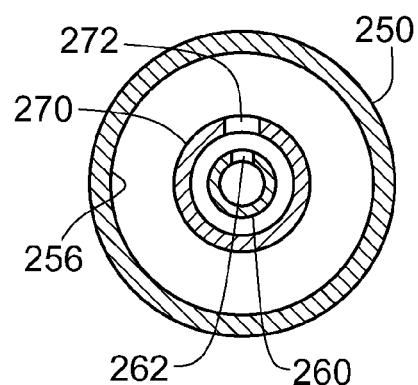
FIG. 34 is a sectional view of the catheter of FIG. 32 taken along line 34-34.

In this second configuration, as shown in FIGS. 32-34, openings 262, 264 of injection tube 260 are aligned with openings 272, 274 of overtube 270. Although only two configurations for the catheter are shown, the injection tube 260 is positionable in any number of locations relative to the fixed overtube 270.

In operation, cryogenic fluid is expelled from the openings and returns to the proximal end of the catheter along a fluid path defined by an inner wall 256 of the outer member 250.

Alternatively, the injection tube 260 and overtube 270 can be provided with multiple openings proximate to and/or aligned with the inner face of one or more thermally-transmissive elements as described earlier herein to achieve more uniform cooling across the entire elongate, thermally-transmissive region.

Figure 35:
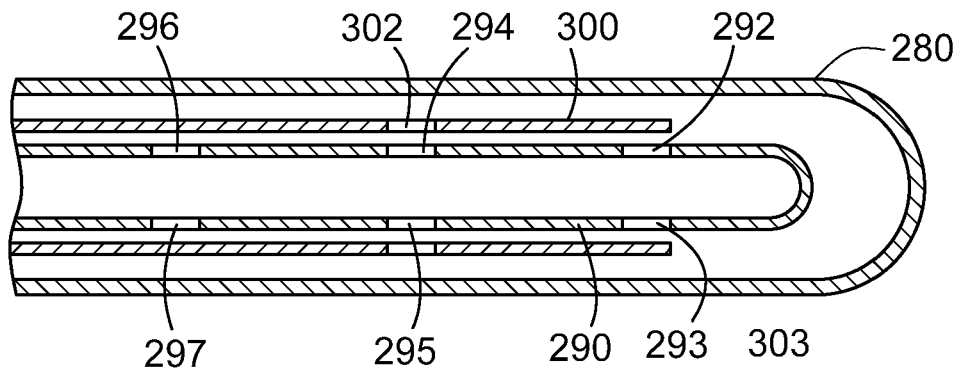
FIG. 35 illustrates yet another embodiment of the catheter.

Referring to FIG. 35, an embodiment of the catheter is illustrated having an outer member 280 with an injection tube 290 with multiple opposed openings 292-297 formed therein. Either the injection tube 290 or the overtube 300 may be slidable in a longitudinal plane to expose and/or cover one or more of the opposed openings on the injection tube 290. For example, as shown in FIG. 35, openings 294, 295 formed on the injection tube 290 are aligned with openings 302, 303 formed on the overtube 230. Furthermore, the injection tube may be positioned in a forwardmost position, not shown, to expose openings on the injection tube proximate the tip of the catheter. In this configuration, the injection tube would provide fluid to cool the area around the tip of the catheter.

In the embodiments described and shown above in FIGS. 32-35, electrode rings as shown in FIG. 25 may be provided along the outer surface of any of the outer members. The electrodes would serve both as electrical conductors and as a thermal transmitter at each location.

Figure 36:
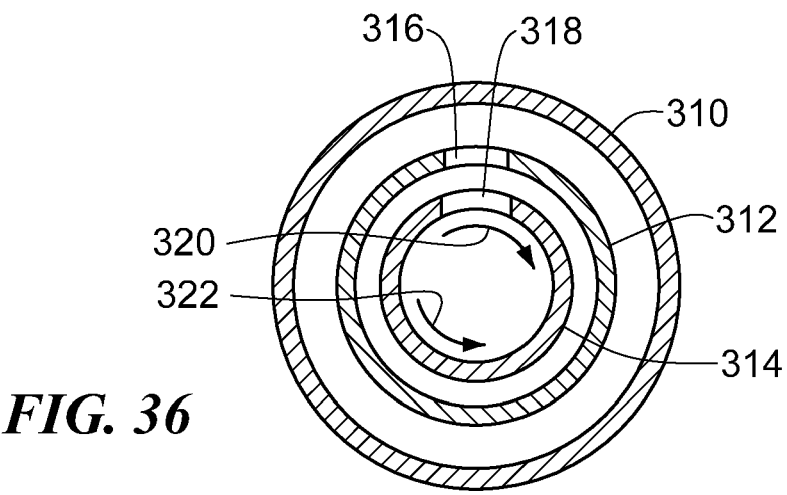
FIG. 36 is a sectional view of yet another embodiment of the catheter.
Figure 37:
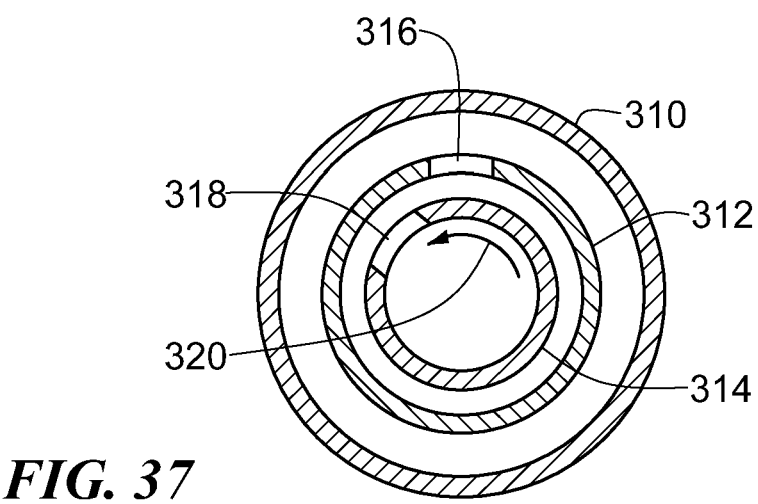
FIG. 37 is a sectional view of the catheter of FIG. 36 after rotation.

Referring to FIGS. 36 and 37, an embodiment of the catheter is illustrated have one or more rotatable members disposed within a flexible outer member 310. In this embodiment, the catheter includes an overtube member 312 and an injection tube member 314, one or both of which are rotatable with respect to one another. In an exemplary embodiment as shown in FIGS. 36 and 37, the injection tube 314 is rotatable relative to the fixed overtube 312. The injection tube 314 may be rotatable in either or both a clockwise and counterclockwise direction as indicated by arrows 320 and 322. As shown in FIG. 36, in a first configuration, opening 316 formed on the overtube 312 aligns with an opening 318 formed on the injection tube 314. As the injection tube 314 is rotated in a counterclockwise direction, the opening 318 on the injection tube 314 is placed out of alignment with the opening 316 formed on overtube 312, as shown in FIG. 37. Alternatively, the injection tube 314 may be fixed in the catheter while the overtube 312 is rotatable. In another embodiment, both the injection tube and overtube may both be rotatable. In yet a further embodiment, the injection tube and/or the overtube are rotatable and slidable within the outer member.

Figure 38:
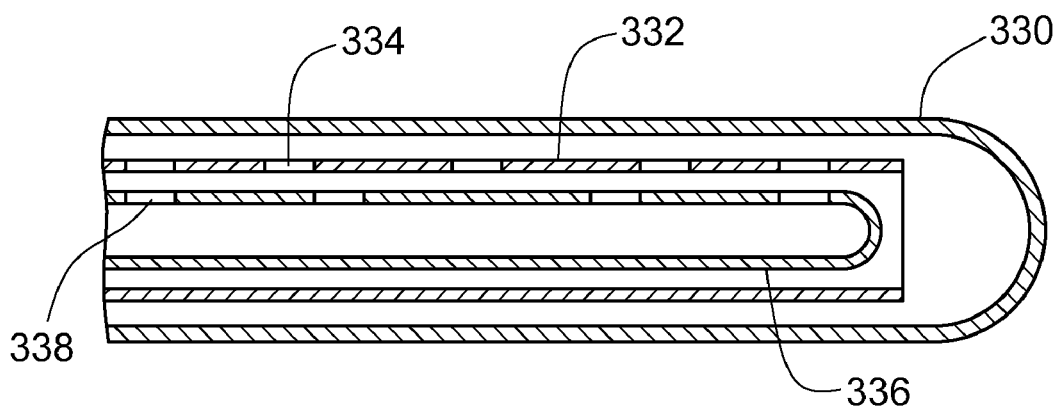
FIG. 38 illustrates yet another embodiment of the catheter.
Figure 39:
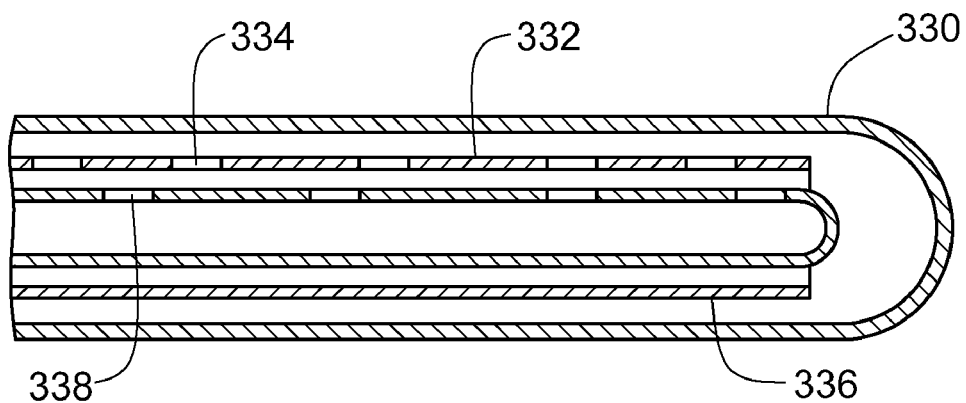
FIG. 39 illustrates the catheter of FIG. 38 in a second configuration.

In the embodiments shown and described above, the slidable and rotatable inner and outer tubes may have openings so arranged as to allow the fluid releasing openings to be in a variety of open and closed configurations with a minimum of relational movement between the tubes. For example, as shown in FIG. 38, an outer member 330 has disposed therein one slidably disposed inner tube 336 which has openings 338 formed thereon in a constant sequence, and a matching slidably disposed outer tube 332 which has openings 334 formed thereon in a constant sequence of slightly different length or intervals. In this configuration, as shown in FIG. 39, small linear relational movements bring the openings on the outer tube 332 and the inner tube 336 into an overlapping configuration.

In addition, the openings as shown and described herein may be so shaped as to allow additional control of fluid release. For example, an outer hole could be tear-shaped and match up with an inner opening that is tear-shaped rotationally aligned 180' oppositely not shown. As the two narrow ends begin to overlap with slidable motion, a tiny aperture is created. With further slidable motion in the same direction, larger areas of the two openings overlap and larger volumes of cryogenic fluid can be released.

A variety of modifications and variations of the present invention are possible in light of the above teachings. Specifically, although many embodiments are illustrated being slender and flexible, other embodiments may be thick and rigid, and introduced into the body directly through incisions or through structures such as trocars. The opening and closing of the catheter openings may also be controlled by using nanotechnology and miniaturized valving. Furthermore, although some of the illustrated devices are particularly well suited for cardiac procedures, the same embodiments and others are equally suited to other organs and/or any body portion that would benefit from the application of thermal energy. For example, the illustrated devices may be used for treating arteries for restenosis or portions of the GI tract to stop bleeding or portions of the GU tract to treat spasm, inflammation, obstruction or malignancy. Thus, the devices as shown are not to be limited to catheters but should be viewed more broadly as cryogenic structures or portions thereof. It is therefore understood that, within the scope of the appended claims, the present invention may be practiced otherwise than as specifically described hereinabove. All references cited herein are expressly incorporated by reference in their entirety.

What is claimed is:

1. A medical system, comprising:
   a cryogenic cooling structure including a tip element having at least two thermally-transmissive segments that are generally cylindrical in shape;
   a sensor coupled to the tip element;
   a source of cryogenic fluid in fluid communication with the cooling structure; and
   a controller in communication with the sensor, the controller programmed to regulate delivery of the cryogenic fluid to the cooling structure in response to a signal from the sensor.

2. The system according to claim 1, wherein the controller is programmed to increase a pressure of the fluid delivered to the tip element based at least in part on a the signal.

3. The system according to claim 2, wherein the controller is programmed to increase the pressure by predetermined pressure increments over predetermined time intervals.

4. The system according to claim 1, wherein the controller is programmed to decrease a pressure of the fluid delivered to the tip element based at least in part on a the signal.

5. The system according to claim 4, wherein the controller is programmed to decrease the pressure by predetermined pressure increments over predetermined time intervals.

6. The system according to claim 1, wherein the sensor is a temperature sensor.

7. The system according to claim 6, wherein the controller is programmed to increase a pressure of the fluid delivered to the tip element based at least in part on a sensed temperature.

8. The system according to claim 6, wherein the controller is programmed to decrease a pressure of the fluid delivered to the tip element based at least in part on a sensed temperature.

9. The system according to claim 6, wherein the controller is programmed to regulate delivery of the cryogenic fluid to the cooling structure in response to a sensed temperature and a predefined target temperature.

10. The system according to claim 1, wherein the source of cryogenic fluid includes cryogenic fluid in a liquid state.

11. The system according to claim 1, wherein the source of cryogenic fluid includes cryogenic fluid in a gas state.

12. A medical system, comprising:
    an elongate member having a distal portion including a bellows-shaped, thermally-transmissive region and a fluid path defined therein;
    a temperature sensor in communication with the fluid path;
    a source of refrigerant in fluid communication with the fluid path; and
    a controller in communication with the temperature sensor, the controller programmed to regulate delivery of the refrigerant to the thermally-transmissive region in response to a sensed temperature and a predefined target temperature.

13. The system according to claim 12, wherein the bellows-shaped, thermally-transmissive region is substantially rigid.

14. The system according to claim 12, wherein the bellows-shaped, thermally-transmissive retains a selected shape after being bent.

15. A medical system, comprising:
    an elongate member having a distal portion including a bellows-shaped, thermally-transmissive region and a fluid path defined therein;
    a sensor in communication with the fluid path;
    a source of refrigerant in fluid communication with the fluid path; and
    a controller in communication with the sensor, the controller programmed to regulate delivery of the refrigerant to the thermally-transmissive region in response to a signal from the sensor.

16. The system according to claim 15, wherein the bellows-shaped, thermally-transmissive region is substantially rigid.

17. The system according to claim 15, wherein the bellows-shaped, thermally-transmissive retains a selected shape after being bent.

18. The system according to claim 15, wherein the controller is programmed to increase a pressure of refrigerant by predetermined pressure increments over predetermined time intervals.

19. The system according to claim 15, wherein the controller is programmed to decrease a pressure of refrigerant by predetermined pressure increments over predetermined time intervals.

* * * * *

UNITED STATES PATENT AND TRADEMARK OFFICE
CERTIFICATE OF CORRECTION

| | | |
|---|---|---|
| PATENT NO. | : 8,043,284 B2 | Page 1 of 1 |
| APPLICATION NO. | : 12/792376 | |
| DATED | : October 25, 2011 | |
| INVENTOR(S) | : John W. Lehmann et al. | |

It is certified that error appears in the above-identified patent and that said Letters Patent is hereby corrected as shown below:

In Column 13, at Line 40, delete the word "a".
In Column 13, at Line 46, delete the word "a".

In Column 14, at Line 27, change "thermally-transmissive" to --"thermally-transmissive region"--.

In Column 14, at Line 43, change "thermally-transmissive" to --"thermally-transmissive region"--.

Signed and Sealed this
Seventeenth Day of January, 2012

David J. Kappos
*Director of the United States Patent and Trademark Office*